United States Patent
Missotten et al.

(10) Patent No.: US 9,949,440 B2
(45) Date of Patent: Apr. 24, 2018

(54) SENSOR ARRANGEMENT

(71) Applicant: CNH America LLC, New Holland, PA (US)

(72) Inventors: Bart M. A. Missotten, Winksele (BE); Didier O. M. Verhaeghe, Ypres (BE)

(73) Assignee: CNH Industrial America LLC, New Holland, PA (US)

( * ) Notice: Subject to any disclaimer, the term of this patent is extended or adjusted under 35 U.S.C. 154(b) by 1241 days.

(21) Appl. No.: 14/043,538

(22) Filed: Oct. 1, 2013

(65) Prior Publication Data
US 2014/0090568 A1 Apr. 3, 2014

(30) Foreign Application Priority Data

Oct. 1, 2012 (BE) .................................. 2012/0652

(51) Int. Cl.
A01F 15/08 (2006.01)
B30B 15/28 (2006.01)
G01N 19/02 (2006.01)

(52) U.S. Cl.
CPC .......... A01F 15/08 (2013.01); A01F 15/0825 (2013.01); B30B 15/281 (2013.01); G01N 19/02 (2013.01)

(58) Field of Classification Search
CPC .... A01F 15/08; A01F 15/0825; B30B 15/281; G01N 19/02
See application file for complete search history.

(56) References Cited

U.S. PATENT DOCUMENTS

| 2,758,536 | A | | 8/1956 | Laucck | |
| 2,868,535 | A | * | 1/1959 | Ruge | G01G 3/1408 177/134 |
| 4,106,267 | A | | 8/1978 | White | |
| 4,750,418 | A | | 6/1988 | Naaktgeboren | |
| 5,293,007 | A | * | 3/1994 | Darst | G01L 1/2243 177/229 |
| 5,322,104 | A | | 6/1994 | Morey et al. | |
| 5,558,014 | A | | 9/1996 | Robinson | |
| 2005/0247215 | A1 | | 11/2005 | Biziorek et al. | |
| 2011/0239783 | A1 | * | 10/2011 | Kurtz | G01L 5/0009 73/862.041 |
| 2012/0186466 | A1 | * | 7/2012 | Vande Ryse | A01F 15/0825 100/43 |
| 2012/0240797 | A1 | | 9/2012 | Veraeghe et al. | |

FOREIGN PATENT DOCUMENTS

FR 2360413 A1 3/1978

* cited by examiner

Primary Examiner — Jimmy T Nguyen
Assistant Examiner — Gregory Swiatocha
(74) Attorney, Agent, or Firm — Patrick M. Sheldrake

(57) ABSTRACT

An agricultural baler having a baling chamber, an intake duct leading into the baling chamber and a stuffer mechanism for transferring slice of crop in the intake duct into the baling chamber, wherein the baler comprises a wall segment positioned substantially in line with an inner wall surface of the baler, the wall segment being suspended from the inner wall surface via at least one load measurement sensor in such a manner that both a load perpendicular to, and a load parallel to the inner wall are derivable.

18 Claims, 3 Drawing Sheets

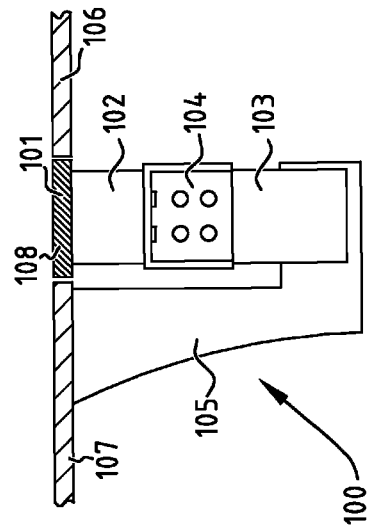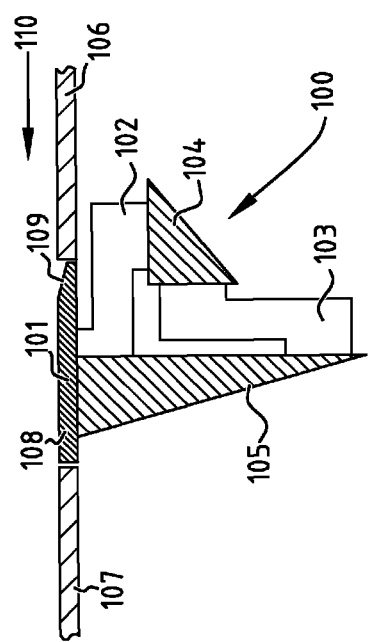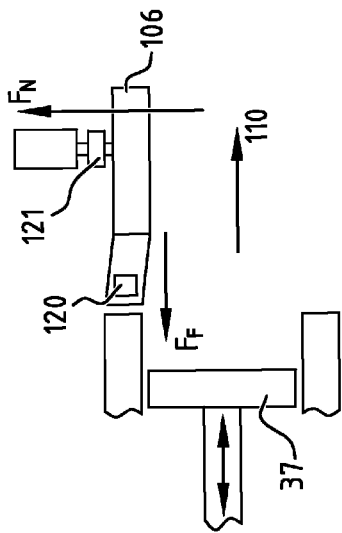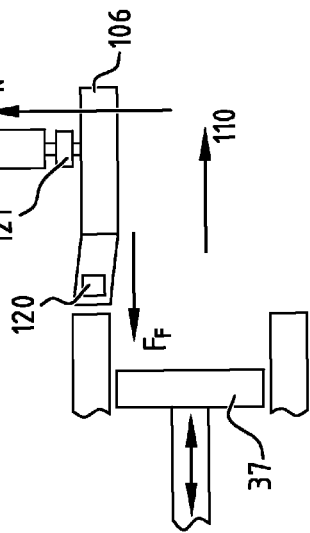

SENSOR ARRANGEMENT

CROSS REFERENCE TO RELATED APPLICATIONS

This Patent Application claims priority under 35 U.S.C. § 119 to BE 2012/0652 filed on Oct. 1, 2012 titled, "Sensor Arrangement" and having Bart M. A. Missotten and Didier Verhaeghe as inventors. The full disclosure of BE 2012/0652 is hereby fully incorporated herein by reference.

TECHNICAL FIELD

The present invention relates to agricultural balers for the formation of square bales of crop material, such as hay, straw or silage in a bale chamber.

BACKGROUND ART

In a conventional baler, as shown for example in U.S. Pat. No. 4,106,267, hay, straw, silage or similar crop material that has been previously cut, windrowed or swathed, is picked up from the ground by a pick-up unit, fed into an intake duct by a packer unit and loaded in successive batches or slices into an elongated bale chamber by tines of a stuffer unit in timed sequence with a reciprocating plunger. The plunger compresses the material into bales and, at the same time, gradually advances the bales towards the outlet of the bale chamber. As the bales reach a predetermined length as determined by a metering device, a knotter device is actuated which wraps cord, twine or other flexible binding material around the bale and secures the ends of the binding material together. Instead of a packer it is also known to for example use a rotor cutter that chops the crop material in smaller pieces.

The packer unit or rotor cutter pre-compresses the crop material in the pre-compression chamber against a backstop. The stuffer unit is designed to transfer slices of the crop material quickly into the bale chamber within the short interval during which the reciprocating plunger clears the entrance of the bale chamber. Typically this is accomplished by a fork assembly of which the arms are rotatably connected to cranks, the arms being provided with longitudinally extending slots in which stationary journals are received. A uniform revolution of the cranks makes the arms shift along and pivot about the journals so that the tines of the fork travel along a generally kidney-shaped path with a varying speed. The maximum or peak speed is obtained when the distance between the connection to the cranks and the stationary journals reaches its minimum, since the arms then act as levers with very close fulcrum points. Such a system permits a quick sweep of the material behind the packer unit through the duct and to the entrance of the bale chamber.

This type of stuffer unit and baler was originally designed for the baling of dry, low density material such as straw or hay, but meanwhile there has been an important shift in agriculture from the use of hay to the use of silage. Silage grass can also be baled, but since it has a higher humidity and a higher density than the other crop materials, the load on the components of the stuffer unit and of the baling chamber increases accordingly.

Solutions have been proposed for example in WO2011/012487 by providing a sensor in the baler which measures the frictional properties of the crop. An operator or an automatic control system can take the output of this friction sensor into consideration so that overload can be avoided.

A drawback from the known sensor is that a change in an external parameter of the crop material such as humidity, density, pressure, etc. significantly changes the load measured via the sensor. As a result, the output of the sensor is not reliable in itself and it requires a complex automatic control system or an experienced operator to correctly interpret the measured load in the context of the external parameters.

It is an object of the present invention to provide a sensor which is less influenced by external parameters, and which provides a reliable output.

Therefore the invention proposes an agricultural baler having a baling chamber, an intake duct leading into the baling chamber and a stuffer for transferring slice of crop in the intake duct into the baling chamber, wherein the baler comprises a wall segment positioned substantially in line with an inner wall surface of the baler, the wall segment being suspended from the inner wall surface via load measurement means in such a manner that both a load perpendicular to, and a load parallel to the inner wall are derivable from the load measurement means.

According to the invention, a normal force (force directed perpendicular to the surface) and a friction force (force parallel to the surface) is measured simultaneously on one wall segment. Thereby, not only the friction force (as is known from the prior art) but also the coefficient of friction is directly derivable from the measurement results. The coefficient of friction can be defined as the friction force divided by the normal force. Unlike the friction force, which is dependent on a multitude of external parameters, the coefficient of friction is a property of the crop material and therefore a more reliable value. As a result, the combination of perpendicular and parallel load measurement proves to be a reliable parameter for an automated control system or for an operator because this combination gives an objective crop-related parameter. An inner wall surface of the baler is defined as one of the boundary surfaces of the baling chamber, such as a sidewall surface, a top surface, a bottom surface or the like.

Preferably, the load measurement means comprise at least two load cells positioned at an angle with respect to one another so that a load measurement in two directions is derivable. A load cell is known in the art and is provided to measure the load in one direction. By having two load cells positioned at an angle with respect to each other, a load in two directions can be measured. Thereby it is noted that the measured directions not need to be the perpendicular and the parallel directions, because via mathematical conversion, the latter directions can be calculated from measurement results in other directions. Preferably, said angle is about 90 degrees as this reduces the margin of error in the conversion and thereby provides in more reliable measurement results.

Preferably, said load cells are moment compensating load cells. Moment compensating load cells are known in the art and are particularly useful in the present situation where multiple load cells are connected. The moments of torque directly acting on the wall segment, and the moments or torque as a result of a cascade of load cells can be compensated thereby not disturbing the load measurements.

Preferably, the wall segment, the two load cells and the inner wall surface of the baler are serially connected. This provides in a mechanically simple and compact solution to measure loads in two directions on one suspended wall segment.

Preferably, the load parallel to the inner wall derivable from the load measurement means is furthermore parallel to a moving direction of crop material in the baling chamber in use. In the moving direction, the highest friction force is measured as this is the direction of movement. In a direction perpendicular to the moving direction, no noteworthy friction force will be measured. In directions between the latter two, proportional forces will be measured. Therefore the margin of error in the calculation of the coefficient of friction is minimized by measuring the friction force in the direction of movement of the crop material.

Preferably, the wall segment has a crop-contacting-surface larger than 50 cm$^2$ and smaller than 1000 cm$^2$, preferably larger than 100 cm$^2$ and smaller than 500 cm$^2$. If the wall segment is too small, the measurement does not represent the average situation in the baler, but only a very local situation (which can deviate from the average). If the wall segment is large, high forces are exerted on the wall segment so that a heavy and rigid construction is necessary to prevent damage. The proposed surface area proves to provide a balance between the magnitude of the forces and the reliability of the measurement. A reliable average measurement values can be derived without unnecessarily high forces on the surface of the wall segment.

Preferably, the wall section is positioned to have its center in a region adjacent and behind a bend in the inner surface of the baling chamber. The bend in the inner surface of the baling chamber is a known aid in the pressing of bales, whereby the crop is first compressed to a maximum (at the bend) and than by the resilience of the compressed crop material, the bale is allowed during the further movement of the baling chamber to relax a bit so that a stable and solid bale is obtained at the end of the baling process. The area after the bend has proven to be the location where a reliable average measurement can be made which is representable for the situation inside the baling chamber.

In another embodiment of the invention, a movable wall section of the baling chamber integrally forms said wall segment by suspending the movable wall section to a frame of the baler via said load measurement means. The movable wall section is already suspended with respect to the inner walls of the baler. By providing load measurement means to the movable wall section which is already suspended, a reliable measurement can be obtained without significant structural amendments to the baler. Preferably, the movable wall section is connected to the baler frame via a hinging mechanism comprising a first load cell provided for measuring the force exerted parallel to the movable wall section, and wherein an actuator, mounted to the movable wall section for moving the latter, is provided with a second load cell provided for measuring the force exerted perpendicular to the wall segment. The hinging mechanism and the actuators form the intermediary elements via which the movable wall section is suspended, and mounting the load measurement means to these elements requires less amendments to the baler structure.

Preferably, a position sensor is provided for measuring the angular position of said wall segment with respect to the moving direction of the plunger of the baler.

The position of the wall segment with respect to the moving direction of the plunger of the baler has an influence on the ratio of load in the perpendicular and the parallel direction. In the case where the wall segment is parallel with the moving direction of the plunger, the direct influence of the plunger force on the perpendicular load measured via the wall segment is negligible. In another case where the angular position of the wall part with respect to the moving direction of the plunger is for example 10 degrees, the direct influence of the plunger force on the perpendicular load measured via the wall segment is quite substantial. Therefore knowing the angular position of the wall segment with respect to the moving direction of the plunger provides advantages in interpreting the load measurements of the wall segment.

An agricultural baler in accordance with the present invention will now be described in further detail, by way of example, with reference to the accompanying drawings, in which.

FIG. 3$a$ is a sideview and FIG. 3$b$ a frontview of an example of a wall segment and load measurement means according to the invention;

FIG. 4 is a topview of a baling chamber comprising a wall segment according to an example of the invention; and FIG. 5 is a topview of a baling chamber comprising another embodiment of a wall segment and a load measurement means according to the invention.

The terms "front", "rear", "forward", "rearward", "left" and "right" used throughout this description are determined with respect to the normal direction of travel of the machine in operation. However they are not to be construed as limiting terms.

Figure 1:
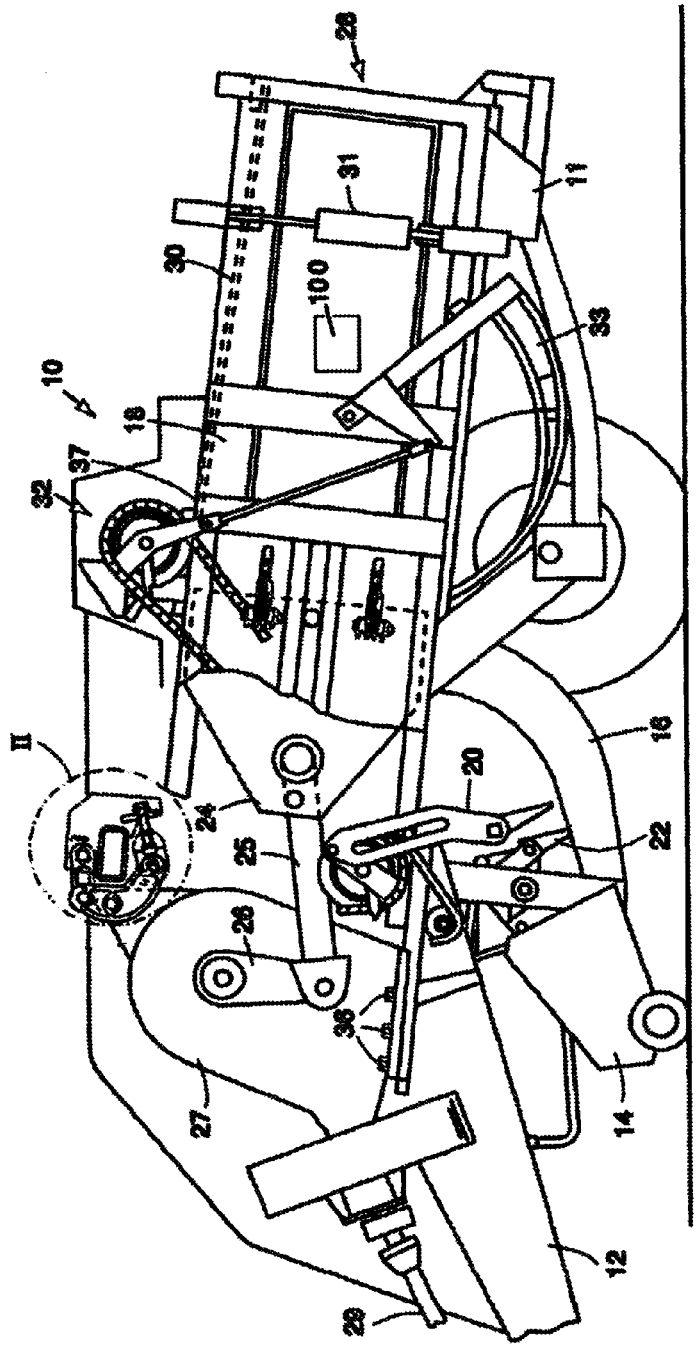
FIG. 1 is a diagrammatical, partly sectional side view of a rectangular baler.

FIG. 1 shows an agricultural baler 10 comprising a main frame 11 which is equipped with a forwardly extending tongue 12 provided at its front end with hitch means (not shown) for coupling the baler 10 to a towing tractor. A pick-up assembly 14 lifts windrowed crop material off the field as the baler 10 is traveled thereover and delivers such material into the front end of a rearwardly and upwardly curved, slice-forming feeder duct 16. The duct 16 communicates at its upper end with an overhead, fore-and-aft extending baling chamber 18 into which slices of crop material are loaded by a cyclically operating stuffer mechanism 20. A continuously operating packer mechanism 22 at the lower front end of the feeder duct 16 continuously feeds and packs material into the duct 16 as to cause charges of the crop material to take on and assume the internal configuration of the duct 16 prior to periodic engagement by the stuffer 20 and insertion up into the baling chamber 18. The feeder duct 16 may be equipped with means (not shown) for establishing whether a complete slice has been formed therein and operating the stuffer 20 in response thereto. Each action of the stuffer 20 introduces a "slice" or "flake" of crop material from the duct 16 into the baling chamber 18.

A plunger 24 reciprocates in a fore-and-aft direction within the baling chamber 18 under action of a pair of connecting or pitman rods 25 (also known as conrods) which are linked to the crank arms 26 of a gearbox 27 driven by a transmission shaft 29 which is connected to the PTO shaft of the tractor. The reciprocating plunger 24 pushes each new slice introduced into the baling chamber 18 rearwardly and forms the subsequent slices into a parallelepiped package of crop material, which is forced by the same action of the plunger 24 toward a rearmost discharge aperture 28 of the chamber.

The baling chamber 18 comprises at least one movable wall portion 30 of which the position can be adjusted to vary the cross section of the aperture 28. Reduction of this cross section will increase the resistance to rearward movement of the crop packages and hence increase the density of the crop material contained therein. Similarly an enlargement of the cross section will reduce said resistance to rearward movement and hence equally reduce the density of the newly formed packages. The position of the wall portion 30 is controlled by actuator means comprising of a pair of hydraulic cylinders 31 (only one shown in FIG. 1) which are installed between the frame 11 and the wall portion 30.

Before leaving the confines of the baler 10, each package is securely bound in its final compacted form by a tying mechanism 32. The length of each bale produced by the baler 10 can be adjustably predetermined by conventional means not shown. The tying mechanism 32 comprises a series of periodically actuated needles 33 which are normally stationed in a stand-by condition below the chamber 18 but which, when actuated, swing upwardly through and across the baling chamber 18 to present twine to a corresponding series of knotters positioned on top of the chamber 18 and extending across the width of the latter.

FIG. 1 shows a wall segment 100 located in a side wall of the baling chamber. Wall segment is placed with respect to the baling chamber so that the surface of the wall segment is in line with the inner surface of the baling chamber. According to the invention, multiple wall segments can be formed inside the baling chamber, inside the intake duct, or at other locations in the agricultural baler.

Figure 2:
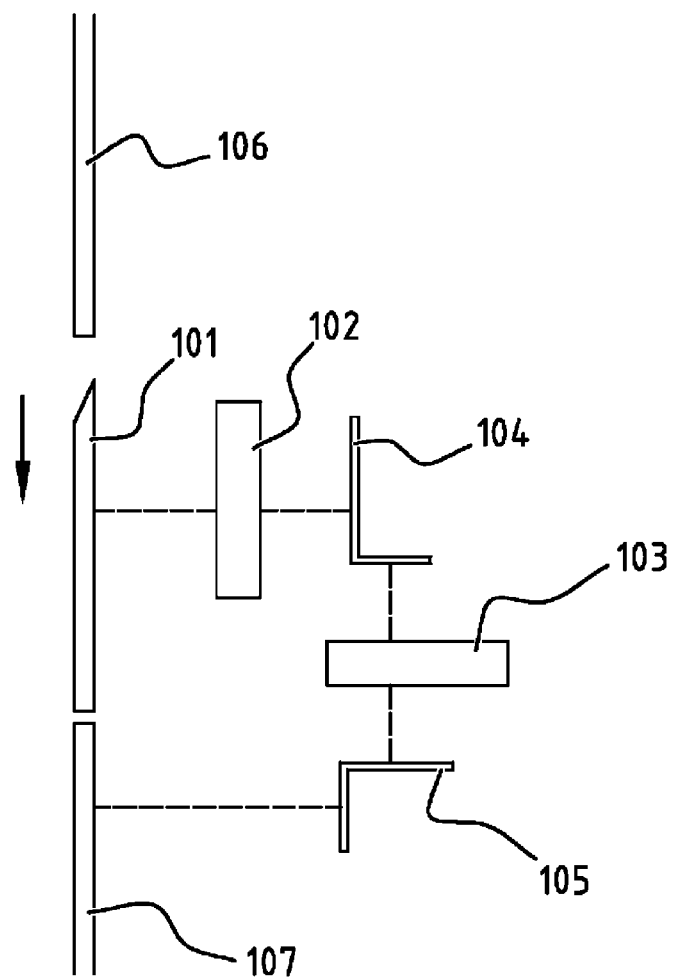
FIG. 2 is a schematic view of a wall segment and load measurement means according to the invention.

FIG. 2 shows a schematic overview of a wall segment 101 that is directly connected to a first load cell 102. The first load cell 102 is further connected to a right-angle-connector 104, the latter interconnecting the first load cell 102 with the second load cell 103. The second load cell 103 is furthermore connected to the inner wall 107 via a connection arm 105.

FIG. 3 shows a wall segment 101 that is suspended to the inner surface 106, 107 of the agricultural baler, via load measurement means. The wall segment has a crop contacting surface 108 provided for contacting the crop material moving through the baling chamber or the intake duct of the agricultural baler. This can be seen in FIG. 3, the wall segment is mounted with respect to the inner wall of the baler 106 in such a manner that the crop contacting surface 108 is in line with the inner surface 107 of the baling chamber wall 106. Preferably, the wall segment is beveled at the front side 109 of the wall section, in such a manner that crop material moving in the moving direction 110 is guided via the beveled front end 109 of the wall segment to slide over this wall segment. This beveled front end 109 thereby prevents crop material from getting choked at the gap between inner wall of the baler and the wall segment.

The wall segment is suspendedly mounted to the inner wall of the baler via load measurement means. Thereby, the wall segment can be directly mounted to the inner wall of the baler, or be mounted to the frame of the baler to which frame the inner wall of the baler is also connected. In the shown figure, the wall segment is connected to the inner wall of the baler. The wall segment is connected to a first load measurement cell 102. This load measurement cell is provided to measure the force parallel to the wall segment. This first measurement cell is connected to a second measurement cell 103 via an intermediary piece 104, so that the second measurement cell is positioned at an angle with respect to the first measurement cell. Preferably, the intermediary piece 104 forms an angle of about 90°, so that the second load measurement cell 103 measures the load perpendicular to the first measurement cell 102. Thereby, the second measurement cell 103 measures the load perpendicular to the wall segment 101. The second load measurement cell is connected to the inner wall 106, 107 of the baler via a second intermediary piece 105.

Although it is claimed that a load parallel to the wall segment and the load perpendicular to a movable load section is derivable from the measurement means, this does not mean that the load measurement cells should directly measure forces in these directions. It will be clear that the measurement cells 102, 103 can be placed under different angles with respect to each other and with respect to the wall segment, and still keeping the capability of deriving the force parallel and perpendicular to the wall segment via mathematical conversion from the measured values. To be able to convert the measurements to a parallel and perpendicular load, the measurement load cells should be placed under an angle of at least 10° one with respect to the other. Preferably the load measurement cells are placed under an angle of at least 25°, more preferably at least 50°, most preferably around 90°. Therefore multiple configurations of load measurement cells can be formed and can all result in the effects of the invention. In the example shown in FIG. 3, load measurement cells are used which are capable of measuring the load in only one direction, and therefore two load measurement cells are used. However one could also use a load measurement cell that is provided to measure the load in two or three directions, so that only one load measurement cell is necessary to measure the loads exerted on the wall segment to derive a parallel and perpendicular load there from.

Preferably the load measurement cells are moment compensation load measurement cells meaning that the load measurement cells are designed so that a moment of torque exerted on the wall segment does not effect the load measurement measured via the load measurement cells 102, 103. Such moment compensating load measurement cells enhance correctness and relevance of the measurement.

FIG. 4 shows a top view of a baling chamber, and shows a plunger that is provided for reciprocally moving and thereby pushing the crop material in direction 110. Thereby, the movable wall part 106 of the inner wall of the baling chamber is provided with a wall segment 101. Via the wall segment 101, a normal force $F_N$ and a friction force $F_F$ is derived from the measurement. The normal force $F_N$ represents the force exerted by the crop material in a direction perpendicular to the wall segment. The friction force $F_F$ is the force parallel to the wall segment and preferably parallel to the moving direction of the crop material 110 and thereby indicates the drag exerted by the crop material to the wall segment resulting from a forward movement 110. The combination of the force $F_F$ and $F_N$ allows to calculate the coefficient of friction. The coefficient of friction can be calculated by dividing the friction force $F_F$ by the normal force $F_N$. The coefficient of friction is a dimensionless scalar value which depends on the materials used, in the present case the crop material and the wall segment material.

Because the coefficient of the friction is material dependent, this value can be used by the agricultural baler to automatically detect the crop material that is processed. If a coefficient of friction is calculated of around 0.25, the crop material can be for example very dry straw. In another example, if the calculated coefficient of friction is around 0.7, the crop material can be wet silage. Various coefficients of friction can be associated with a look-up table with various crop materials. Preferably, the baler comprises a moisture sensor for measuring the moisture of the crop material. The results from this moisture measurement can also be used in combination with the calculated coefficient of friction to increase the chance of successful crop material detection. Furthermore the measurement results of the wall segment 101 can be used for overload protection. Should a high normal force be measured, the data processor of the agricultural baler can be programmed to stop plunger movement or to open the movable wall section 106 so that the pressure level inside the baling chamber is decreased.

Preferably the angular position of the wall segment is measured via an angular sensor. In the embodiment of FIG. 4, the angular sensor can be constructed as part of the hinging mechanism of the movable wall section 106. Thereby, the angular sensor is provided for measuring the angular position of the wall segment with respect to the moving direction 110 of the crop material. This angular position influences the load measured via the wall segment 101. Namely, when the angular position of the wall segment with respect to the crop material moving direction 110 is zero, meaning that the wall segment is in line with the moving direction 110 of the crop material, then the normal force does not comprise a noteworthy part of the plunger force. However if the angular position of the wall segment with respect to the moving direction 110 of the crop material is for example 10°, then the direct influence of the plunger force on the wall segment is sin (10°)=17% of the plunger force. Therefore, this angular position is preferably transferred to the data processor of the agricultural baler, so that the latter can take this angular position into account when interpreting the measured loads for recommending actions. The angular sensor can alternatively be integrated into the actuator means controlling the position of the movable wall section 106. Thereby, the extent that the actuator is extended is proportional to the angular position of the wall segment. As a further alternative, a distance sensor can be provided at the movable wall section to measure the distance between the movable wall section and a reference point on the baler frame, the distance being proportional to the angular position of the movable wall section.

FIG. 5 shows an alternative embodiment, whereby the movable wall section 106 integrally forms the wall segment according to the invention. To this end, the movable wall section 106 is suspended with respect to the baler frame via load measurement means 120, 121 whereby first load measurement means 120 is integrated into the hinging mechanism and measures the friction force $F_F$. The second load measurement means 121 is integrated into the actuator, for measuring the normal force $F_N$ exerted to the movable wall section 106. Thereby, an angular position sensor can be integrated into the hinging mechanism to measure the angular position of the movable wall section 106.

The wall segment according to the invention can be used in the agricultural baler in various ways, for example by the data processor to recommend actions to the operator or to steer different actuators and system inside the agricultural baler. Thereby, an advantage is that both a friction force and a normal force is measured via the same wall segment. Therefore the coefficient of friction can be calculated. This coefficient of friction can be used in the density control system of the agricultural baler to control the density of the bales formed in the baler. Thereby, preferably a moisture sensor and a angular position sensor measuring the angular position of the wall segment with respect to the moving direction 110 of the crop material is also coupled to the density control system.

The manner in which the data processor arrives at a recommended action is not fundamental to the present invention. It may simply rely on values derived from a look-up table in which the stored values have been determined empirically or it may employ a mathematical algorithm that generates suitable settings for the various parameters. As a further possibility, the data processor may employ a so-called expert system which essentially learns to avoid past mistakes.

When a group of suitable control parameter settings is determined by the data processor, the desired settings are compared with the actual setting and a recommended action is taken by the data processor to change the parameter that differs most from the desired settings. Preferably, the data processor changes the parameter to a value halving the difference between its current setting and the desired setting determined by the data processor.

The square baler according to the invention as defined in the claims is of course not limited to the exemplary embodiments as described and shown in the drawings, but can equally comprise combinations and variations that fall within the scope of protection of the claims.

The invention claimed is:

1. An agricultural baler, comprising:
    a baling chamber;
    an intake duct leading into the baling chamber;
    a stuffer mechanism for transferring slice of crop in the intake duct into the baling chamber; and
    a wall segment positioned substantially in line with an inner wall surface of the baling chamber, the wall segment being suspended from the inner wall surface via a load measurement assembly, the load measurement assembly comprising:
        a first load measurement sensor directly connected to the wall segment at one end and connected to a first intermediary piece at another end; and
        a second load measurement sensor connected to the first intermediary piece;
    wherein a load parallel to the inner wall surface is derivable from the first load measurement sensor, and
    wherein a load perpendicular to the inner wall surface is derivable from the second load measurement sensor.

2. The agricultural baler according to claim 1, wherein the first and second load measurement sensors comprise two load cells positioned at an angle with respect to one another so that a load measurement in two directions is derivable.

3. The agricultural baler according to claim 2, wherein said angle is about 90 degrees.

4. The agricultural baler according to claim 2, wherein said load cells are moment compensating load cells.

5. The agricultural baler according to claim 2, wherein the two load cells are serially connected.

6. The agricultural baler according to claim 5, wherein the first intermediary piece is a right-angle-connector.

7. The agricultural baler according to claim 1, wherein the wall segment, the first and second load measurement sensors, and the inner wall surface of the baler are serially connected.

8. The agricultural baler according to claim 7, wherein the second load measurement sensor is connected to the inner wall surface via a second intermediary piece.

9. The agricultural baler according to claim 1, wherein the load parallel to the inner wall surface, derivable from the first load measurement sensor, is parallel to a moving direction of crop material in the baling chamber.

10. The agricultural baler according to claim 1, wherein the wall segment has a crop-contacting-surface larger than 50 $cm^2$ and smaller than 1000 $cm^2$.

11. The agriculture baler according to claim 1, wherein the wall segment is positioned to have its center in a region adjacent and behind a bend in the inner surface of the baling chamber.

12. The agriculture baler according to claim 1, wherein a movable wall portion of the baling chamber integrally forms said wall segment by suspending the movable wall portion to a frame of the baler via said at least one load measurement sensor.

13. The agriculture baler according to claim 10, wherein said at least one load measurement sensor comprises at least a first load cell and a second load cell and the movable wall portion is connected to the baler frame via a hinging mechanism comprising the first load cell provided for measuring the force exerted parallel to the movable wall portion, and wherein an actuator, mounted to the movable wall portion for moving the latter in a transverse direction, is provided with the second load cell for measuring the force exerted substantially perpendicular to the wall segment.

14. The agriculture baler according to claim 1, wherein a sensor is provided for measuring the angular position of said wall segment with respect to the moving direction of the plunger of the baler.

15. The agricultural baler according to claim 1, wherein the wall segment has a crop-contacting-surface larger than 100 cm² and smaller than 500 cm².

16. The agricultural baler according to claim 1, wherein the first intermediary piece is an L-shaped connector.

17. The agricultural baler according to claim 1, comprising a second intermediary piece defining an L-shaped connector connecting the second load measurement sensor to the inner wall surface.

18. A method of measuring loads in an agricultural baler including a baling chamber, an intake duct leading into the baling chamber, and a stuffer mechanism for transferring slice of crop in the intake duct into the baling chamber, the method comprising:

suspending a wall segment from an inner wall surface of the baling chamber via a load measurement assembly, the wall segment positioned substantially in line with the inner wall surface of the baling chamber and the load measurement assembly comprising (i) a first load measurement sensor directly connected to the wall segment at one end and connected to a first intermediary piece at another end, and (ii) a second load measurement sensor connected to the first intermediary piece;

deriving a load parallel to the inner wall surface from the first load measurement sensor; and driving a load perpendicular to the inner wall surface from the second load measurement sensor.

* * * * *